(12) United States Patent
Melcher

(10) Patent No.: US 8,092,843 B2
(45) Date of Patent: Jan. 10, 2012

(54) METHOD AND COMPOSITION FOR CUTANEOUS TREATMENT OF HERPES SIMPLEX INFECTIONS

(75) Inventor: Gordon Melcher, Henerson, NV (US)

(73) Assignee: East Park Research, Inc., Las Vegas, NV (US)

( * ) Notice: Subject to any disclaimer, the term of this patent is extended or adjusted under 35 U.S.C. 154(b) by 98 days.

(21) Appl. No.: 12/565,126

(22) Filed: Sep. 23, 2009

(65) Prior Publication Data

US 2011/0070321 A1    Mar. 24, 2011

(51) Int. Cl.
*A61K 36/886* (2006.01)
*A61K 36/534* (2006.01)

(52) U.S. Cl. .................... 424/744; 424/747
(58) Field of Classification Search .......... None
See application file for complete search history.

(56) References Cited

U.S. PATENT DOCUMENTS

| | | | | |
|---|---|---|---|---|
| 4,309,989 A * | 1/1982 | Fahim | .............. | 601/2 |
| 4,670,265 A * | 6/1987 | Sydiskis et al. | .............. | 424/744 |
| 5,714,150 A * | 2/1998 | Nachman | .............. | 424/769 |
| 6,117,844 A * | 9/2000 | Fredrickson | .............. | 514/27 |
| 6,455,580 B1 | 9/2002 | Fredrickson | | |
| 6,632,798 B2 | 10/2003 | Hamdi et al. | | |
| 2007/0299045 A1 * | 12/2007 | Gershon | .............. | 514/184 |

OTHER PUBLICATIONS

Hershoff et al. Herbal Remedies: A Quick and Easy Guide to Common Disorders and their Herbal Remedies. Penguin. 2001. Page number not provided. 1 page.*
Piret et al. Efficacies of Topical Formulations of Foscarnet and Acyclovir and of 5-Percent Acyclovir Ointment (Zovirax) in a Murine Model of Cutaneous Herpes Simplex Type 1 Infections. Anti Microbial Agents and Chemotherapy. vol. 44. No. 1. pp. 30-38.*
Conrick. Neem: The Ultimate Herb. Lotus Press. 2001. p. 17.*

* cited by examiner

*Primary Examiner* — Melenie McCormick
(74) *Attorney, Agent, or Firm* — Dennison, Schultz & MacDonald

(57) ABSTRACT

A method for cutaneous treatment of Herpes simplex infections by applying topically to the area of outbreak a composition comprising at least 1% by weight D-Lenolate® olive leaf extract. A composition for treatment is also disclosed, containing, by weight, at least 1% D-Lenolate® olive leaf extract, 1-3% neem, 0.05-1% aloe and 0.05-1% menthol.

3 Claims, 2 Drawing Sheets

METHOD AND COMPOSITION FOR CUTANEOUS TREATMENT OF HERPES SIMPLEX INFECTIONS

BACKGROUND OF THE INVENTION

Paralleling the human immunodeciency virus (HIV) epidemic, there is growing number of both men and women infected with Herpes simplex virus type-1 (HSV-1) and Herpes simplex virus type-2 (HSV-2). HSV-1 causes mostly sores in the facial area (Herpes facialis), while in rare cases can cause severe encephalitis and blindness. HSV-2 causes infections in the genital organs (Herpes genitalis). In recent years an increasing number of cases have been reported with HSV-1 infections in the genital areas, while HSV-2 has been also increasingly isolated from facial sores indicating that these viruses can efficiently infect both sites. Both viruses have the ability to become latent (no virus production) in sensory ganglia and to induce recurrent infections following reactivation from external stimuli including stress, ultraviolet irradiation, immunosuppression and others causes. More than forty-five million Americans are currently infected with life-long infections of HSV-2. Seroprevalence rates range from 60-80% in developing countries, while in the US, HSV-2 seropositivity is approximately 23% in women and 11% in men. Overall, epidemiological studies have shown that HSV infection increases the risk of HIV-1 infection. These studies strongly suggest the need for the development of topical microbiocides to combat both infections.

During the past several decades, acyclovir has been the drug of choice for the treatment of herpetic infections. However, an increasing number of viral strains that are resistant to acyclovir inhibition has been reported, especially for immunocompromised individuals and organ and bone transplant recipients. Other drugs that work in a similar fashion with acyclovir to inhibit virus replication include foscarnet (trisodium phosphonoformate), which has a broad antiviral spectrum and in vitro activity against all human viruses of the herpes virus family, including cytomegalovirus, HSV, and varicella zoster virus. However, foscarnet intravenous administration has been reported to cause increased nephrotoxicity and other adverse reactions.

Topical formulations currently available to treat herpes infections include 5% acyclovir ointment (Zovirax®) and penciclovir cream (Vectavir® or Denavir®). These formulations have been noted to have limited efficacy, particularly against symptomatic recurrent herpes. Specifically, treatment of recurrent herpes with topical acyclovir demonstrated no or only limited clinical benefit.

A number of natural and readily available non-toxic synthetic compounds have been reported to have antiviral activities against Herpes simplex infections.

Cimetadine, an inexpensive OTC drug with potential immune enhancing properties, has been reported to have antiviral activity against both herpes simplex and herpes zoster viruses.

Coconut oil is thought to lyse lipid coated viruses such as the HSV and HIV viruses that contain a viral envelope.

Antiviral properties have been also attributed to vitamin A, vitamin C and zinc in combination, thought to result from enhancement of the immune responses against Herpes viruses.

BHT, an inexpensive food preservative and antioxidant, inactivates the Herpes virus (and other lipid coated viruses) by solubilizing the lipid coating around the virus.

Lysine supplements and diets with a high lysine/arginine ratio are believed by many to inhibit herpes virus replication.

Garlic and propolis have been also reported to have antiviral activities.

In most instances, scientific information about the antiviral properties of these compounds is rather limited. However, a number of over-the-counter products have been launched and are currently available based on rather anecdotal information about the antiviral properties of these compounds.

U.S. Pat. No. 6,455,580 discloses oral and parenteral administration of oleuropein, an olive leaf extract, for treatment of viral diseases, including Herpes.

U.S. Pat. No. 6,632,798 discloses administration of oleuropein for inhibiting angiogenesis, and for treatment thereby of a wide variety of diseases. Among the diseases mentioned are diseases associated with corneal neovascularization, including Herpes simplex and Herpes zoster infections.

SUMMARY OF THE INVENTION

It is therefore an object of the invention to provide a method and composition for treatment of cutaneous Herpes simplex infections with a safe and readily available over-the-counter medication.

To achieve this and other objects, the invention is directed to a method for cutaneous treatment of Herpes simplex infections by applying topically to the area of outbreak a composition comprising at least 1% by weight D-Lenolate® olive leaf extract.

D-Lenolate® olive leaf extract is a mixture of compounds extracted from olive leaves by the method disclosed in U.S. Pat. No. 5,714,150, incorporated herein by reference, and containing about 30-40% by weight of oleuropein. The extract is obtained by multiple alcoholic extractions of olive leaves, followed by distillation under vacuum to obtain a concentrate which is dried, 8 with all steps taking place at about 20-88° C.

Specifically, the extract is obtained by a method comprising the steps of treating olive leaves with an alcohol and water solution to produce an alcoholic extract, draining the alcohol and water solution from the olive leaves, treating the olive leaves with fresh alcohol and water solution at least two more times, combining the alcoholic extracts produced and distilling the combined extracts under vacuum at a temperature of about 20° C. to 88° C. to produce a concentrated extract having a solids content of about 30-40%. 40%. The concentrated extract can then be spray dried or oven dried under vacuum to produce a dry powder extract comprising approximately 30-40% by weight oleuropein.

Preferably, the composition applied to the outbreak contains at least 2% by weight of D-Lenolate® olive leaf extract.

A preferred composition for application comprises, by weight, 2-3% D-Lenolate® olive leaf extract, 0.2-3% neem, 0.05-1% aloe and 0.05-1% menthol, in an inert gel vehicle, for example polyoxypropylene and polyoxyethylene in a concentration of 16% by weight suspended in phosphate buffered saline (PBS).

BRIEF DESCRIPTION OF THE DRAWINGS

FIG. 2 includes five graphs of animal survival in percent vs. time post infection (in days), each graph including one treatment composition and a PBS control, in which:

Figure 1:
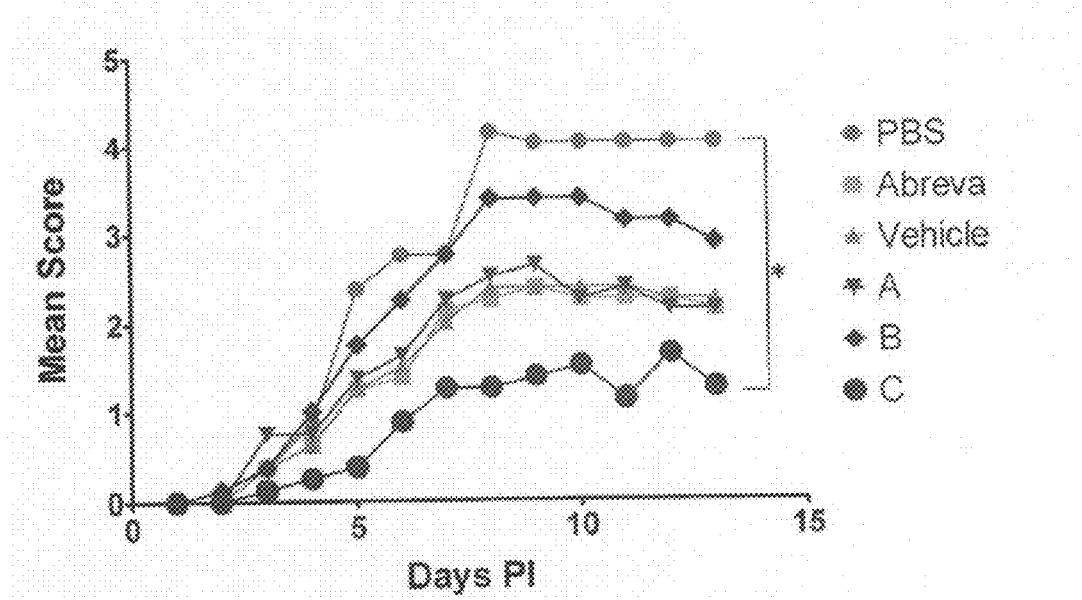
FIG. 1 is a graph of mean scores per treatment group vs. time post infection (in days) for herpes treatments and controls.

A shows an Abreva® treatment;
B shows a treatment with the vehicle without any active ingredient;
C shows Dose A treatment;
D shows Dose B treatment; and
E shows Dose C treatment.

DETAILED DESCRIPTION OF THE INVENTION

There is extensive experience with murine models studying immune responses to pathogens and testing various antiviral formulations. This experience, combined with the low cost and the availability of a wide array of reagents, suggests that the mouse provides an optimal model to study the effectiveness of topical microbiocides against Herpes simplex infections, as well as the ensuing mucosal changes. In the study reported herein, the hairless mouse system was used as a model of cutaneous Herpes simplex infection. Skin lesions in hairless mice are comparable to "cold sores" or fever blisters in man. In hairless mice, infection leads to cutaneous lesions at the site of infection. Eventually the animal dies due to the high level of challenge virus and the absence of circulating antibodies in the animals at the time of the infection. Progressive infection provides an easy method to determine the efficacy of antiviral compounds for the treatment of cutaneous herpes infections.

Clinical disease progression, virus replication and pathological changes were monitored daily. The antiviral and healing properties of the compounds tested and controls were assessed and reported.

The following procedure was used:

Infection of mice by scarification: A location on the backs of the mice between the third and fourth lumbar vertebrae was scarified with a blunted gauge needle giving a cross-hatched pattern. The scarified areas were approximately 1 cm in diameter. Twenty µl of HSV-1 (GKAB-1) virus stock containing approximately $5 \times 10^5$ PFU was applied on the scratched area using a pipettor. The degree of infection in hairless mice is readily scored by severity and extent of the lesion using a scale of 0-4 or by mortality rates.

Treatments: Three formulations containing D-Lenolate® olive leaf extract, as well as positive and negative controls, were applied topically at the infection site as a gel base (formulation mixed with inert gel material). The compositions are set forth in Table 1, below (% by weight).

TABLE 1

|  | Dose A | Dose B | Dose C |
| --- | --- | --- | --- |
| D-Lenolate ® olive leaf extract | 0.2 | 0.6 | 2.0 |
| Neem | 0.2 | 0.6 | 2.0 |
| Aloe | 0.05 | 0.15 | 0.5 |
| Menthol | 0.05 | 0.15 | 0.2 |
| Gel Base | Remainder | Remainder | Remainder |

Dose A was the most effective mixture determined in an in vitro model. Dose B is a 3× concentration of D-Lenolate® olive leaf extract and other components and have the minimal concentration of monograph active ingredients. Dose C is a 10× concentration of D-Lenolate® olive leaf extract and other components have at least the minimal concentration of monograph active ingredients.

These compositions were prepared by mixing together appropriate amounts of stock solutions prepared from powdered extracts which were re-suspended in PBS, vortexed and centrifuged under sterile conditions. The cleared supernatants were filtered and maintained under sterile conditions.

The gel vehicle was prepared by slow dissolving of Pluronic F-127 in DMEM (Dulbecco's Modified Eagle Medium) at 4° C.

Sterile supernatants were added to the inert gel vehicle composed of polyoxypropylene and polyoxyethylene suspended in phosphate buffered saline (200 mM, pH 6.0) at a concentration of 18% (wt/wt). A pH of 6.0 was used to correspond to the pH of the skin.

The treatment schedule for the animals was started at 12 hours after inoculation of virus and every 8 hours afterward to mimic application schedules for human patients.

Groups of animals (10 mice per group) were tested as follows:
1. Uninfected mice without receiving any treatment.
2. Uninfected mice treated with dose A in vehicle.
3. Uninfected mice treated with dose C in vehicle.
4. Infected mice without receiving any treatment.
5. Infected mice treated with Abreva® (an OTC topical antiviral containing Docosanol, also known as behenyl alcohol) at 12 hours post infection.
6. Infected mice treated with dose A in vehicle at 12 hours post infection.
7. Infected mice treated with dose B in vehicle at 12 hours post infection.
8. Infected mice treated with dose C in vehicle at 12 hours post infection.

A total of 80 mice were used for this experiment.

Skin lesions: Skin lesions usually appeared at 12-48 hours following infection. Initial lesions appeared as punctate erosions in the area of the dermatome involved. The relative proximity to the site of scarification varies from one animal to another. The lesions typically enlarged within two or three days and in latter stages of the infection form unilateral band-like lesions which subsequently ulcerate. In animals that recover, lesions healed within two weeks. In most instances, paralysis of the lower legs preceded systemic infection and death. Treatment of animals was continued until all or the majority of the animals in the untreated group developed lesions or died.

Virus strain: HSV-1 strain F (American Type Culture Collection, Manassas, Va.) was propagated in Vero (African green monkey kidney) cells (American Type Culture Collection) in Eagle's minimum essential medium (Invitrogen, Inc.), supplemented with 0.22% sodium bicarbonate, 100 U of penicillin-streptomycin per ml, 2 mM L-glutamine, and 2% fetal bovine serum (EMEM 1 2% FBS) to obtain a viral inoculum of $1.5 \times 10^6$ PFU/ml.

Animal model details: Female hairless mice (SKH1; 6 weeks old; Charles River Breeding Laboratories Inc.) were used throughout this study. Mice were anesthetized using 2-3% isoflurane. The virus was inoculated on the lateral side of the body in the left lumbar skin area. The skin was scratched six times in a crossed hatch pattern with a 27 needle held vertically. A viral suspension ($5 \times 10^5$ PFU/50 µl) was rubbed for 10 to 15 seconds on the scarified skin area with a cotton tipped applicator saturated with EMEM and 2% FBS. The scarified area was protected with a corn cushion (Schering-Plough, Inc.), which was held on the mouse body with surgical tape. The porous inner wall of the aperture of the corn cushion was made impermeable with tissue adhesive (Vetbond, St. Paul, Minn.) prior to use to prevent drug absorption by the patch, which could act as a reservoir due to the accumulation of drug formulations. The aperture of the corn cushion was also closed with surgical tape. Mice were then returned to their cages and observed twice daily.

Treatments: For treatments initiated at early times post infection (i.e., prior to the appearance of the zosteriform rash), the surgical tape closing the aperture of the corn cushion was removed and the scarified area wiped with a sterile gauze pad to be evaluated by viral titer, and cleaned with a cotton-tipped applicator saturated with sterile cold water to remove gel or ointment remaining from the last application. Fifteen microliters of the base alone, Abreva®, or base containing the compound mixture was applied to the scarified area. The aperture of the corn cushion was closed with surgical tape to avoid systemic administration that could result from licking and grooming. Three daily treatments were given at 8:00 AM, 2:00 PM, and 9:00 PM, as these times represent convenient times for self-application by patients.

The efficacies of the different treatments were evaluated by use of lesion scores, survival rates, and viral titers in skin samples.

Determination of viral titers in skin samples: The extent of inhibition of HSV-1 replication in skin samples of mice was determined every 8 hours post virus inoculation for 48 hours and on the 3 and 5 day by swabbing the site of the virus inoculation with a sterile gauze pad. The swabs were placed in PBS solution and stored at 5° C. after vigorous mixing. Virus titers were evaluated after limiting dilution of the PBS solution on Vero cell monolayers.

Statistical analysis: The areas under the curve (AUC) of the mean lesion scores for the different treatment groups between days 4 and 10 were compared by use of a one-way analysis of variance, followed as appropriate by a t-test with Fisher's corrections for multiple simultaneous comparisons. The significance of the differences in the mortality rates between control and treated groups were evaluated by use of a chi square test. The significance of the differences in the viral titers between infected control and drug-treated groups were analyzed by use of a one-tailed Mann-Whitney U test. All statistical analyses were performed with a computer package (StatMate, LaJolla, Calif.). A P value of less than 0.05 is considered statistically significant.

Results: Mice began to develop detectable lesions at sites of infection on day 2 post-infection with a majority showing signs of infection by day 4. The lesions were scored as follows:

Early/low scoring lesions were typically characterized by discreet vesicular eruptions associated with dermal scarifications. These eruptions subsequently darkened and were easily visible by day 5 post-infection (Score 1).

Individual eruptions would then merge to form scabbed over bands (Score 2). Lateral lesion spread and/or banding occurred when secondary eruptions appeared outside the area defined by the initial site of infection.

In more advanced cases, lesion banding spread to define a dermatome extending from the site of infection down the outside of the left leg. Subsequent dermatome expansion onto the paw was often accompanied by leg retraction and paw curling, along with secondary lesion development on the left ventral posterior abdomen proximal to the vagina and anus (Score 3).

Extreme cases (Score 4) involved distal lesion development across the anterior-posterior midline from the SOI. Cross-midline lesions could appear on either dorsal or ventral surfaces. Cross midline lesions were frequently a prelude to more severe complications leading to euthanasia.

Animals that presented with hind limb paralysis, severe weight loss, or signs of dehydration were given scores of 5 and euthanized.

By day 15, all surviving mice showed visible signs of improvement reflected in declining lesion scores.

Analysis: Lesion scores for individual mice were plotted vs. days post-infection and the area under the curve (AUC) for each animal was determined. The Mean AUC for each treatment group was calculated from days 1-13 and plotted vs. time post infection, as shown in FIG. 1.

One-way ANOVA with Bonferroni's correction for multiple comparisons showed that the experimental treatments had a significant effect on the mean AUC. Individual unpaired two tailed t-tests using Welch's correction for unequal group variances showed that treatment with the highest d-Lenolate concentration (Dose C) significantly reduced the mean AUC as compared with all other treatments excluding Abreva. The difference between the mean AUC of the PBS control-treatment group and the mean AUC of the Dose C group was highly significant (two-tailed t test p value=0.0031).

Figure 2:
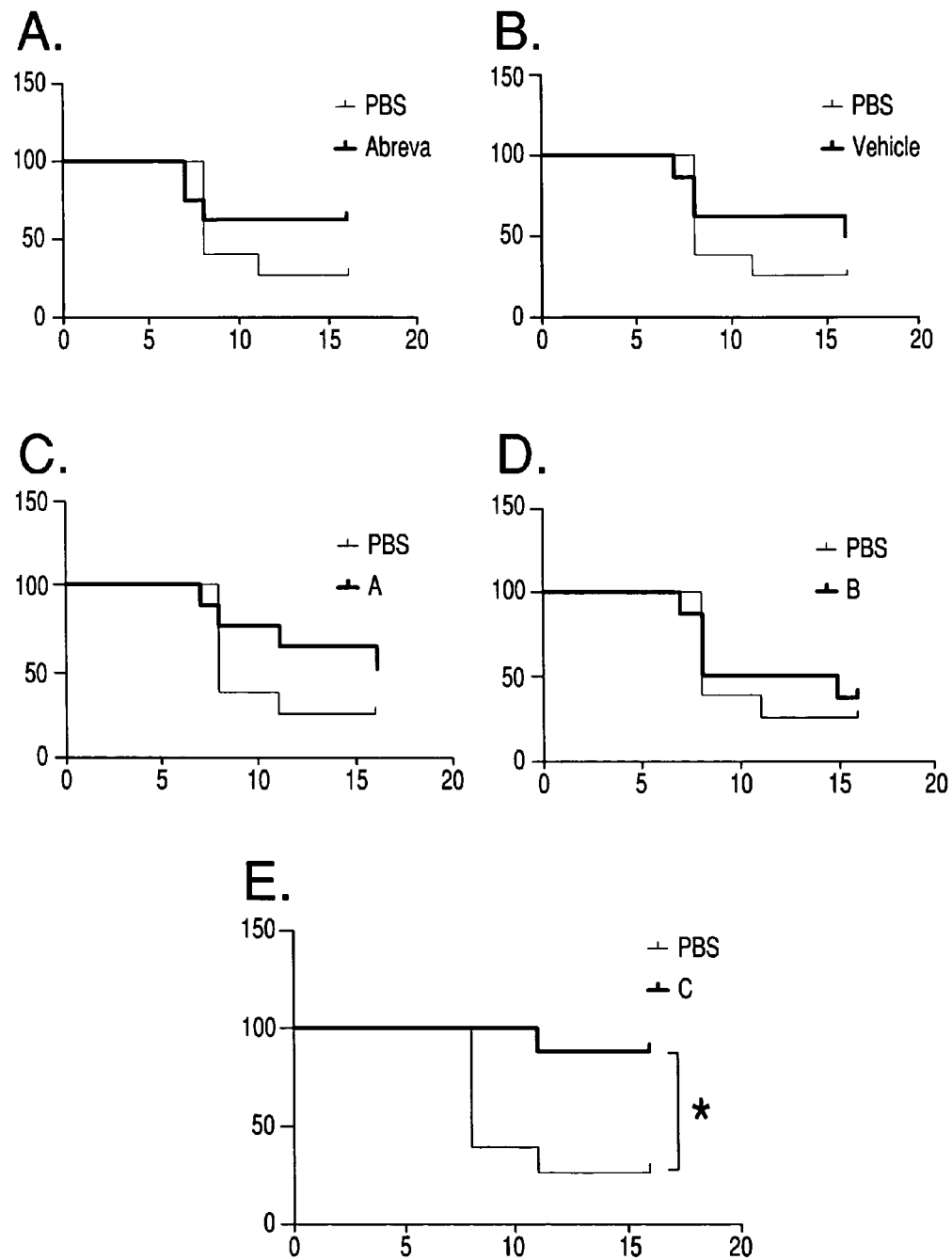

These results were also supported by analysis of animal survival data. Mean survival curves were established for each group and are shown in FIG. 2, plotted as percent survival over time (days post infection). The survival curve for each experimental group is shown alongside the survival curve derived from the PBS-treated control group for comparison. Survival curves of the experimental treatments were compared with that derived from PBS treatment using Log-rank (Mantel-Cox) and Gehan Breslow-Wilcoxon tests. The results from these tests agree that mortality was significantly reduced in groups receiving treatment with Dose C (p values 0.0088 and 0.0069 respectively), while other treatments displayed no significant differences in mortality.

Controls in this experiment behaved as expected. Herpes lesion and symptom development in mice treated with PBS were the most rapid and the most severe. Surprisingly however, treatment with Abreva® had, at best, a minimal effect on Herpes symptom development and duration. Treatments with the lower doses of D-Lenolate® olive leaf extract (Doses A and B) did not display any measurable therapeutic effect under the conditions of this study. In contrast, treatment with Dose C was clearly effective in mitigating and ameliorating herpes disease symptoms.

Conclusions: There were no significant differences between any of the mean AUCs for groups treated with PBS, vehicle with no active ingredient, Dose A and Dose B. In other words this study was unable to detect any effect of these treatments on Herpes infection in the SKH1 murine model. In contrast, the Dose C experimental treatment group presented with significantly reduced symptoms, characterized not only by a decrease in the number of animals with herpes symptoms, but also a decrease in mortality and in the severity of disease in symptomatic animals. Statistical analyses support this conclusion; p values calculated for the comparison of herpes lesion scores and mortality between dose C and PBS treatments suggest that the observed differences are highly significant.

It was clear from this study that treatment with D-Lenolate® olive leaf extract in a sufficient concentration inhibits human herpes simplex virus pathogenesis in the SKH1 murine skin model.

What is claimed is:

1. A method for cutaneous treatment of herpes simplex infections comprising topically applying to an area of outbreak a composition comprising about 2% by weight of an olive leaf extract, about 2% by weight neem, about 0.5% by weight aloe and about 0.2% by weight menthol, wherein the olive leaf extract contains 30-40% by weight oleuropein and is obtained by a method which comprises performing multiple alcoholic extractions of olive leaves to obtain multiple alcoholic extracts, combining the alcoholic extracts, distilling the combined alcoholic extracts under vacuum to obtain a concentrated extract having a solids content of about 30-40%, the extractions and distillation taking place at 20-88° C., and drying the concentrated extract under vacuum to obtain the olive leaf extract containing 30-40% by weight oleuropein.

2. A method according to claim 1, wherein the Herpes simplex is Type-1.

3. The method according to claim 1, wherein the composition additionally comprises an inert gel vehicle comprising polyoxypropylene and polyoxyethylene, suspended in phosphate buffered saline (PBS).

* * * * *